United States Patent
Looten et al.

(10) Patent No.: US 9,315,434 B2
(45) Date of Patent: Apr. 19, 2016

(54) METHOD FOR PREPARING A COMPOSITION RICH IN LUTEIN PRODUCED BY MICROALGAE

(71) Applicant: ROQUETTE FRERES, Lestrem (FR)

(72) Inventors: Philippe Looten, Lomme (FR); Samuel Patinier, Quesnoy-sur-Deule (FR); Eric Francais, Voinemont (FR); Michel Perrut, Villers les Nancy (FR); Aurore Satre-Buisson, Champigneulles (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/420,136

(22) PCT Filed: Aug. 7, 2013

(86) PCT No.: PCT/FR2013/051902
§ 371 (c)(1),
(2) Date: Feb. 6, 2015

(87) PCT Pub. No.: WO2014/023917
PCT Pub. Date: Feb. 13, 2014

(65) Prior Publication Data
US 2015/0225322 A1    Aug. 13, 2015

(30) Foreign Application Priority Data

Aug. 8, 2012 (FR) ...................... 12 57691

(51) Int. Cl.
| | |
|---|---|
| C07C 29/86 | (2006.01) |
| A23L 1/30 | (2006.01) |
| C09B 61/00 | (2006.01) |
| C12P 23/00 | (2006.01) |
| C07C 403/24 | (2006.01) |
| C12N 1/06 | (2006.01) |
| A61K 31/047 | (2006.01) |

(52) U.S. Cl.
CPC . *C07C 29/86* (2013.01); *A23L 1/30* (2013.01); *A23L 1/3002* (2013.01); *A61K 31/047* (2013.01); *C07C 403/24* (2013.01); *C09B 61/00* (2013.01); *C12N 1/066* (2013.01); *C12P 23/00* (2013.01); *A23V 2002/00* (2013.01); *C07C 2101/16* (2013.01); *Y02P 20/544* (2015.11)

(58) Field of Classification Search
None
See application file for complete search history.

(56) References Cited

U.S. PATENT DOCUMENTS

| | | | |
|---|---|---|---|
| 5,714,658 A | 2/1998 | Heidlas et al. | |
| 7,329,789 B1 * | 2/2008 | Schonemann | ........ C07C 403/24 210/634 |

FOREIGN PATENT DOCUMENTS

| | | |
|---|---|---|
| EP | 0761765 | 3/1997 |
| EP | 1808483 | 7/2007 |
| FR | 2924126 | 5/2009 |
| WO | WO 2004/094350 | 11/2004 |
| WO | WO 2010/128957 A1 * | 11/2010 ............ C07C 403/24 |
| WO | WO 2012/064186 | 5/2012 |

OTHER PUBLICATIONS

Kitada et al., Journal of Chemical Technology and Biotechnology (2009), 84(5), pp. 657-661.*

* cited by examiner

*Primary Examiner* — Brian J Davis
(74) *Attorney, Agent, or Firm* — Saliwanchik, Lloyd & Eisenschenk

(57) ABSTRACT

The invention relates to a method for preparing a composition rich in lutein produced by microalgae, particularly microalgae belonging to the *Chlorella* genus, more specifically produced by *Chlorella vulgaris*, characterized in that said method includes the sequence of the following steps: 1) preparing a cell lysate from the microalgae biomass; 2) treating the lysed microalgae biomass with a polar solvent, preferably ethyl acetate, in order to obtain an oleoresin containing the lutein and the lipids from the initial biomass; 3) extracting the oleoresin obtained in step 2) by means of a non-polar solvent, here a fluid at supercritical pressure, in order to obtain a fraction rich in non-polar lipids, mainly consisting of triglycerides, and an insoluble fraction rich in lutein; and 4) recovering the thus lutein-enriched fraction.

14 Claims, 4 Drawing Sheets

METHOD FOR PREPARING A COMPOSITION RICH IN LUTEIN PRODUCED BY MICROALGAE

CROSS-REFERENCE TO RELATED APPLICATION

Figure 1:
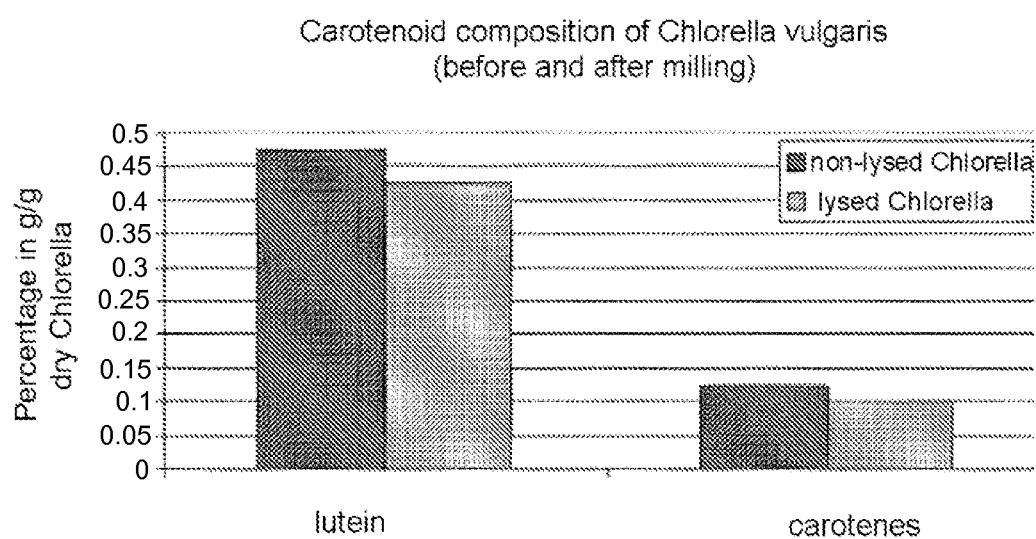

This application is the U.S. national stage application of International Patent Application No. PCT/FR2013/051902, filed Aug. 7, 2013.

FIELD OF THE INVENTION

The present invention relates to a method for obtaining a composition rich in lutein produced by microalgae, more particularly microalgae of the *Chlorella* family, even more particularly produced by *Chlorella vulgaris*.

PRESENTATION OF THE STATE OF THE ART

Carotenoids are somewhat orange or yellow pigments that are widespread in a very large number of living organisms. They are liposoluble and can generally be easily simulated by organisms.

They belong to the chemical family of the terpenoids, formed from the polymerization of isoprene structures with an aliphatic or alicyclic structure. It is generally accepted that they follow metabolic pathways similar to those of lipids.

They are synthesized by all green plants and by many fungi and bacteria (including cyanobacteria) and by all algae. They are absorbed by animals in their food.

Carotenoids have antioxidant properties and have been studied for the prevention of cancer and of other human diseases.

Carotenoids are naturally present in edible leaves, flowers and fruit, and are easily obtained from flowers (for example, marigolds), berries, and root tissues (for example, carrots).

Representative examples of carotenoids include α-carotene, β-carotene and lycopene.

β-Carotene and lycopene are generally present in a free noncombined form, which is trapped within the chloroplasts of plant cells.

Xanthophylls are yellow-colored molecules derived from carotenes, through the addition of oxygen atoms (alcohol, ketone, epoxy, etc. functions).

Xanthophylls are abundant in a certain number of yellow or orange fruits and vegetables, such as peaches, mangoes, papayas, prunes, squashes and oranges.

They are also found in the chloroplasts or the chromoplasts of plant cells, in particular in the petals of certain yellow-, orange- or red-colored flowers, and in algae, for example brown algae (Phaeophyceae), where they mask chlorophyll.

Xanthophylls are antioxidants which contribute, inter alia, to the health of the eyes.

Examples of xanthophylls include lutein, astaxanthin, canthaxanthin, zeaxanthin, cryptoxanthin, etc.

Some xanthophylls are present in flowers of plants, such as marigolds, generally in the form of diesters of adds such as palmitic add and myristic acid.

As a general rule, the free forms of carotenoids are also present in the chloroplasts of green plants such as alfalfa, spinach or curly kale, green leaves and green vegetable matter.

The free form of carotenoids has better absorption when they are consumed in foods or as a food supplement.

Lutein is a xanthophyll pigment of formula 4-[18-(4-hydroxy-2,6,6-trimethylcyclohex-1-en-1-yl)-3,7,12,16-tetramethyloctadeca-1,3,5,7,9,11,13,15,17-nonaen-1-yl]-3,5,5-trimethylcyclohex-2-en-1-ol found in high concentrations in the macula of the eye and in the central part of the retina.

It plays an important role therein in the filtering out of ultraviolet light wavelengths in order to prevent damage to the lens of the eye and to the macula.

Lutein has, moreover, antioxidant properties which also make it possible to protect the macula, which is rich in polyunsaturated fatty acids, against light-induced free radicals.

Lutein cannot be produced by the body and, consequently, must be taken in through the diet.

Thus, lutein has become increasingly used in nutritional supplements for the prevention and/or treatment of loss of vision caused by age-related macular degeneration (or ARMD), cataracts, and retinitis pigmentosa.

The most common source of lutein extracts is precisely the calendula flower, which contains one of the highest known levels of lutein and which has the advantage of containing only a low concentration of the other carotenoids.

Lutein in crystalline form is conventionally obtained from the flowers of the French marigold (*Tagetes erecta*) of the family Asteraceae by extraction with solvents, in order to produce an oleoresin (containing 70% of lutein).

This oleoresin is then purified by carrying out other series of extractions, either with solvents (hexane, pentane, dichloromethane, ethyl alcohol, methanol) or using 1,2-propylene glycol and potassium hydrochloride.

This two-step mode of extraction is, for example, described in international patent application WO 2012/064186.

These two methods result in a final product from which 99% to 99.9% of the organic extraction solvents have been removed.

The crystalline lutein can be incorporated into a suspension of corn oil before being sold.

The methods for purifying lutein, in the form of fatty acid esters, from marigold flower petals, are for example taught in the literature by U.S. Pat. No. 4,048,203, U.S. Pat. No. 5,382,714 and U.S. Pat. No. 5,648,564, in which the dried marigold flower petals are treated with a hydrocarbon-based solvent.

With regard to the extraction of lutein from green plants, it may be advantageous, since it does not require additional chemical steps of saponification and then of lysis in order to release the lutein in free form, said form being desired for better absorption when it is consumed.

However, the extraction and purification of lutein, as well as carotenes and fatty adds, from plants is not very economical because it requires many expensive purification steps and a lot of time in order to separate them from the large amounts of other compounds present in vegetable materials.

Moreover, the lutein content of marigold flowers remains low (0.3 mg/g of dry matter).

There is therefore an increasing interest in using microalgae as an alternative source of this carotenoid.

For example, microalgae of *Muriellopsis* sp., *Chlorella zofingiensis, Scenedesmus almeriensis* and *Chlorella protothecoides* types have already been proposed as potential sources of lutein.

Nevertheless, the lutein productivities described are not sufficiently high to be economically viable on an industrial scale.

Numerous procedures have been described, for example that of international application WO 89/006910, in order to obtain lutein or a lutein-enriched composition from cultured algal cells.

In patent EP 1 808 483, the method more particularly used consists of centrifugation, sedimentation or filtration under vacuum in order to concentrate the cells, and drying of the concentrated cells.

The dried cell biomass is then preferably stored at a low temperature (for example, −20° C. or even lower) in packaging under vacuum or, preferably, through the introduction of nitrogen into the plastic bags in order to remove the oxygen.

Patent EP 1 808 483 also recommends the addition of antioxidants and emulsifiers to the harvested cell suspension.

In addition to the recovery of a lutein-rich biomass, patent EP 1 808 483 describes the possibility of having lutein with better bioavailability. The preferred method then comprises rupturing the collected cells and drying them in order to obtain a lutein or a lutein-enriched composition.

The use of a standard bead mill is recommended, in which the suspension of biomass is disintegrated in suspension in water in the presence of an appropriate antioxidant in order to prevent lutein oxidation.

After drying, a powdered product of the "particles of small size" type is obtained. The powder thus obtained can then be used directly in food applications intended for human consumption, such as food supplements, or used as a mixture with other ingredients, such as fish meal in aquaculture.

In another method, the lutein can be concentrated by means of a method for extraction with nonpolar solvents or supercritical solvents so as to be formulated in food supplements or pharmaceutical products.

The extraction of lutein with nonpolar solvents or with supercritical fluids has especially been described in the plant field.

Thus, for example, in U.S. Pat. No. 6,106,720, a method for extracting carotenoids from algae, from carrot juice or from tomato skin is described, said method comprising the flow of supercritical carbon dioxide presaturated with water in a column under particularly high pressure and temperature conditions (450 to 1200 bar and 50 to 300° C.).

In U.S. Pat. No. 4,632,837, a method for the production of concentrated extracts from fresh plants of culinary herbs such as dill, tarragon leaves and mimosa flowers is described, said method comprising extraction with supercritical $CO_2$ at a temperature of 0 to 40° C. and at a pressure of 80 to 200 bar, and separation of the extract with diethyl ether or pentane at a pressure of 20 to 60 bar and a temperature of 0 to 20° C.

U.S. Pat. No. 4,466,923 describes a supercritical $CO_2$ extraction of lipids from leguminous plant seeds, from cereal germs and from animal meat by simultaneous application of temperatures from 60 to 80° C. and of pressures from 700 to 1200 bar.

U.S. Pat. No. 5,120,558 describes, for its part, a method for extraction from spices such as sage, vanilla, pepper, celery, ginger or cinnamon, said method which uses supercritical $CO_2$ being carried out continuously with four extraction tanks, between 400 and 600 bar and a temperature of 80 to 120° C., and fractionation from spices so as to obtain an oleoresin.

Thus, all these methods have especially been used for higher plants and none of them suggested possible extrapolation of such methods for extraction of lutein from microalgae in general, and from *Chlorella* in particular.

Moreover, it is clearly apparent that these methods suffer from the drawback according to which it is necessary to improve the solvent power of the supercritical fluid, either by implementing high pressure and temperature operating conditions, or by combining it with another nonpolar organic solvent.

Consequently, the underlying problem of the present invention is that of providing an alternative method for obtaining a composition rich in lutein produced by microalgae.

SUMMARY OF THE INVENTION

The subject of the invention is a method for preparing a composition rich in lutein produced by microalgae, more particularly microalgae of the *Chlorella* family, even more particularly produced by *Chlorella vulgaris*, characterized in that it comprises:
1) preparing a cell lysate from the microalgal biomass,
2) treating the lysed microalgal biomass with a polar solvent, in order to obtain an oleoresin containing the lutein and the lipids from the initial biomass,
3) extracting the oleoresin obtained in step 2) by means of a nonpolar solvent, in the form of a fluid at supercritical pressure, in order to obtain a fraction rich in nonpolar lipids, mainly consisting of triglycerides, and an insoluble fraction rich in lutein, and
4) recovering the thus lutein-enriched fraction.

In certain embodiments, the polar solvent of step 2) is chosen from the group made up of alcohols such as methanol, ethanol, n-propanol, isopropanol, butanol or isobutanol, esters such as ethyl acetate, propyl acetate or butyl acetate, and ketones such as acetone, cyclohexanone, methyl ethyl ketone and methyl isobutyl ketone, taken alone or in combination, and is preferably ethyl acetate.

In another embodiment, the method according to the invention is characterized in that the nonpolar solvent in the form of a fluid at supercritical pressure is brought to a pressure of between 10 and 50 MPa, more preferentially between 25 and 40 MPa, and to a temperature of between 35 and 90° C., and preferentially between 40 and 70° C. Preferably, the nonpolar solvent is carbon dioxide.

In step 1), the cell lysate can be obtained by milling a biomass of microalgae of the *Chlorella* family having a dry matter content ranging from 10% to 15% by weight. Before step 2) is carried out, the cell lysate obtained in step 1) can be concentrated to a dry matter content of greater than 15% by weight, preferably ranging from 20% to 30% by weight.

In certain embodiments, step 2) of the method comprises a step of extracting the cell lysate with a polar solvent, preferably ethyl acetate, and a step of removing the polar solvent from the organic phase obtained. Removal of the solvent can be carried out by evaporation under vacuum or at reduced pressure.

A subject of the invention is also a lutein-enriched composition obtained by means of the method according to the invention and the use of said lutein-enriched composition for preparing a pharmaceutical composition, a food supplement or a food.

Finally, an additional subject according to the invention is a method for preparing a composition comprising lutein chosen from a food supplement, a food and a pharmaceutical composition, said method comprising:
a) preparing a lutein-enriched fraction from a microalgal biomass by carrying out the method according to the invention, and
b) obtaining said composition from the lutein-enriched fraction obtained in step a).

FIGURES

FIG. 1 presents the assaying of total carotenoids (carotene and lutein) of *Chlorella vulgaris* before milling (dark grey diagrams) and after milling (light grey diagrams) of the biomass. The results are expressed as mass percentage of lutein or carotene relative to the dry weight of the biomass.

Figure 2:
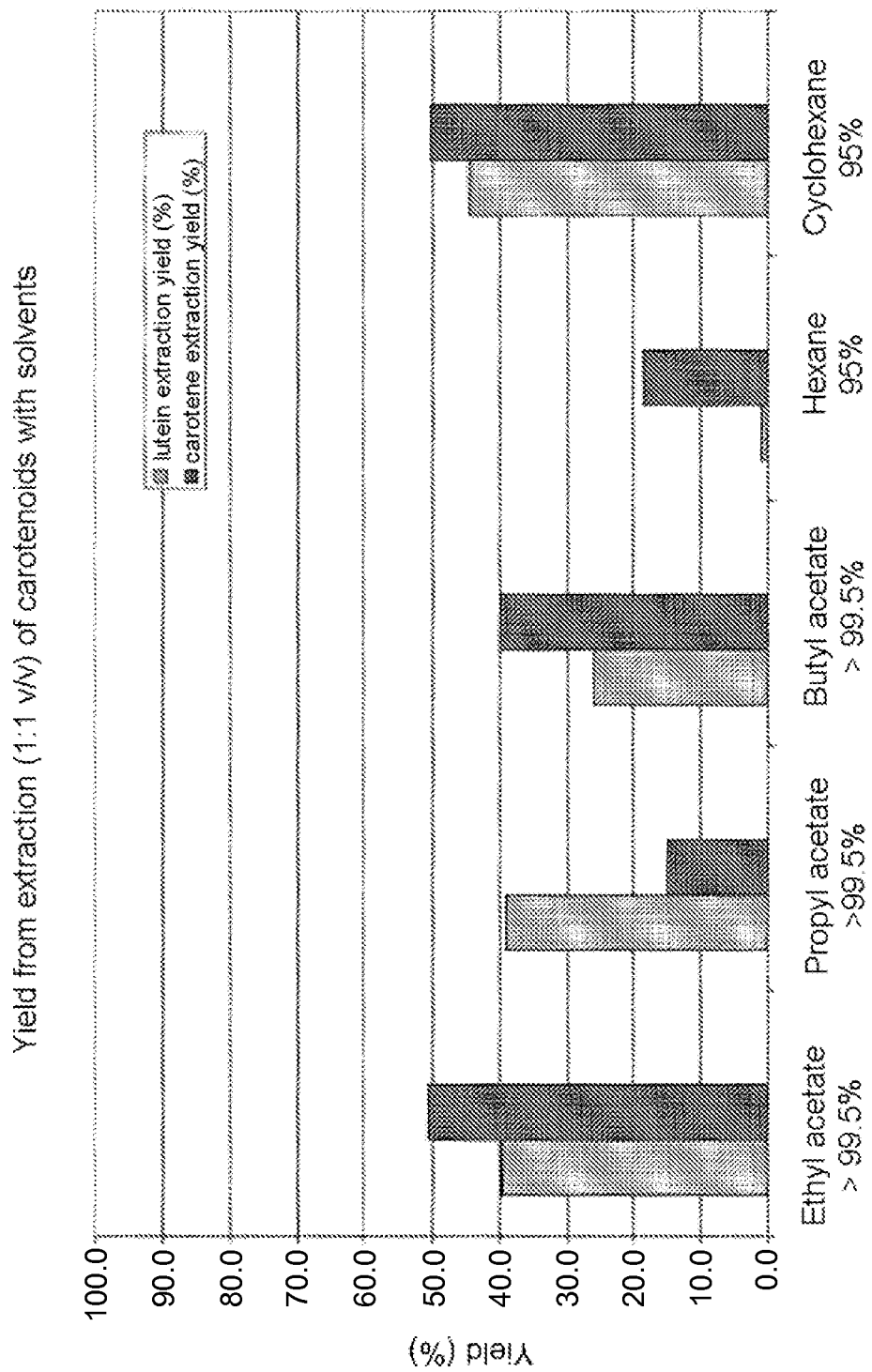

Various extraction solvents were tested for carrying out step 2) of the method. FIG. 2 shows the results of extraction for the lutein (light grey diagrams) and the carotenes (dark grey diagrams) obtained by extraction of the cell lysate with various solvents. From left to right: ethyl acetate, propyl acetate, butyl acetate, hexane and cyclohexanone. The yields are expressed as mass percentage of lutein or of carotene.

Figure 3:
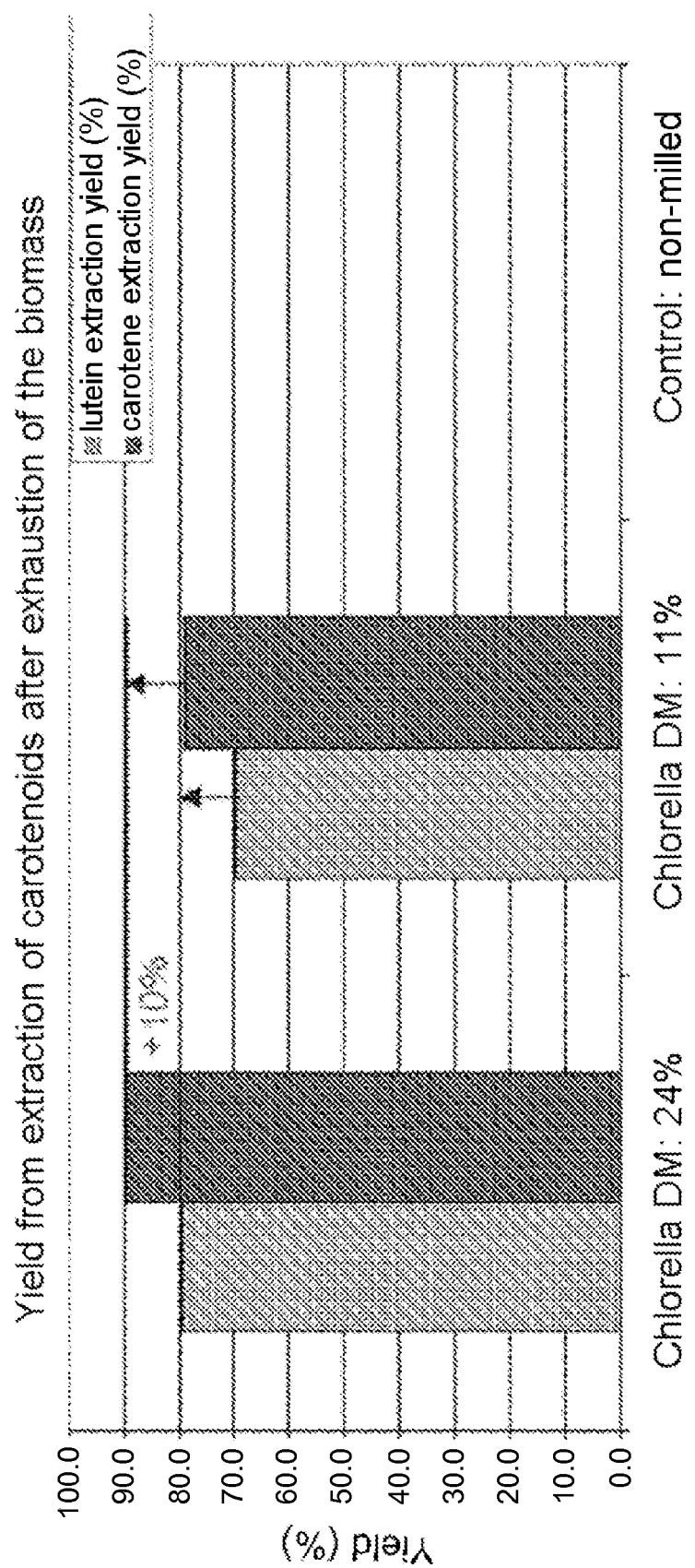

FIG. 3 illustrates the influence of the dry matter content of the cell lysate on the carotene (dark grey diagrams) and lutein (light grey diagrams) extraction yields obtained in step 2). From left to right: concentrated *Chlorella* cell lysate containing 24% of dry matter (*Chlorella* DM: 24%), concentrated *Chlorella* cell lysate containing 11% of dry matter (*Chlorella* DM: 11%) and non-milled non-lysed biomass (control).

Figure 4:
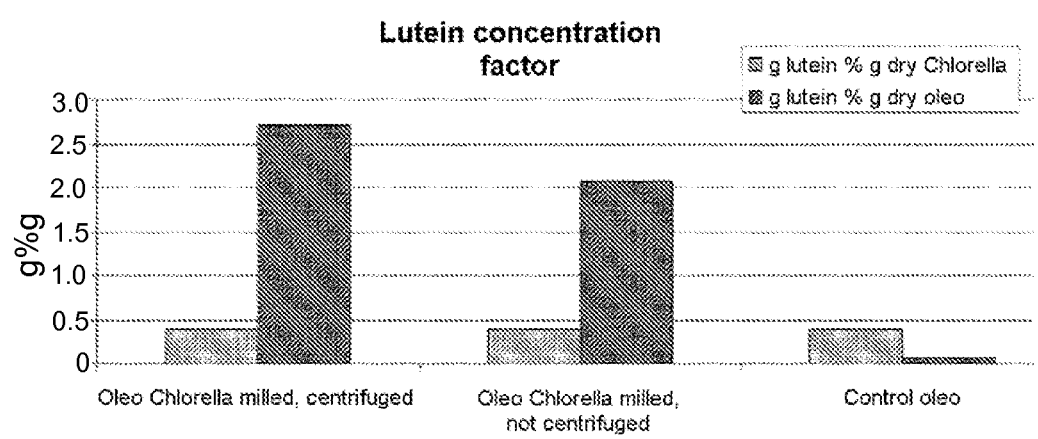

FIG. 4 shows the contents (mass % relative to the dry weight) of lutein in the starting biomasses (light grey diagrams) and in the oleoresins obtained from these biomasses (dark grey diagrams). From left to right: milled and centrifuged *Chlorella* biomass (concentrated cell lysate containing 24% of dry matter (DM)), non-centrifuged, milled *Chlorella* biomass (cell lysate containing 11% of dry matter), non-lysed *Chlorella* biomass (control).

DETAILED DESCRIPTION OF THE INVENTION

Anxious to develop a more effective method for obtaining a composition rich in lutein produced by microalgae, more particularly microalgae of the *Chlorella* family, even more particularly produced by *Chlorella vulgaris*, the applicant company has developed its own research and has succeeded in adapting the supercritical fluid extraction technologies so as to guarantee an enrichment in lutein.

The present invention therefore relates to a method for preparing a composition rich in lutein produced by microalgae, more particularly microalgae of the *Chlorella* family, even more particularly produced by *Chlorella vulgaris*, characterized in that it comprises the sequence of the following steps:
1) preparing a cell lysate from the microalgal biomass,
2) treating the lysed microalgal biomass with a polar solvent in order to obtain an oleoresin containing the lutein and the lipids from the initial biomass,
3) extracting the oleoresin obtained in step 2) by means of a nonpolar solvent, in this case a fluid at supercritical pressure, in order to obtain a fraction rich in nonpolar lipids, mainly consisting of triglycerides, and an insoluble fraction rich in lutein, and
4) recovering the thus lutein-enriched fraction.

The microorganisms are preferentially microalgae belonging to the *Chlorella* family, even more preferentially *Chlorella vulgaris*.

The first step of the method in accordance with the invention therefore consists of preparing a cell lysate of the microalgal biomass.

It is known how to conventionally culture microalgae of the *Chlorella* genus, and more particularly *Chlorella vulgaris*, in closed, generally tubular, photobioreactors where it is possible to inject carbon dioxide in high concentration.

These cultures under autotrophic conditions conventionally make it possible to obtain a concentration of *Chlorella vulgaris* microalgae of about 50 to 80 g/l.

The recovery and concentration of the biomass are then carried out by any means known to those skilled in the art, such as centrifugation.

In the context of the invention, the microalgal biomass thus collected and then concentrated can have a dry matter content of between 10% and 15%, preferably a dry matter content of about 11%.

In order to extract the molecules of interest, including the carotenoids, a cell milling step (i.e., a step of preparing a cell lysate) is often essential.

In order to extract the molecules of interest under non-denaturing conditions, it is preferable to carry out the cell milling, most possibly under cold conditions, under an inert atmosphere and in the dark.

An increased temperature and light are in fact capable of initiating oxidation of the molecules.

Thus, in certain embodiments of the method according to the invention, step 1 comprises preparing a cell lysate from a microalgal biomass by milling. Preferably, the microalgal biomass has a dry matter content ranging from 10% to 15% by weight relating to its total weight. In another preferred embodiment, the milling step is carried out under cold conditions, in the dark and under an inert atmosphere.

The applicant company recommends using bead mill technology, in recirculation or pass mode, as will be exemplified hereinafter. However, in order to increase the molecule-of-interest extraction yields, the milling may be envisioned upon a concentrated microalgal biomass and the milling may be carried out in the solvent phase.

The effectiveness of the milling is monitored under an optical microscope (magnification ×40), the lysis being total when there is no longer any intact cell visible in the field of the microscope.

As will be exemplified hereinafter, this milling step generates only a loss of at most 10% of the total carotenoids.

The second step of the method in accordance with the invention consists of treating the lysed microalgal biomass with a polar solvent in order to obtain an oleoresin containing the lutein and the lipids from the initial biomass.

The term "polar solvent" is intended to mean any solvent which has a non-zero dipole moment.

The polar solvent is chosen from the group consisting of methanol, ethanol, n-propanol and isopropanol, butanol and isobutanol, esters such as ethyl acetate, propyl acetate or butyl acetate, and ketones such as acetone, cyclohexanone, methyl ethyl ketone and methyl isobutyl ketone, taken alone or in combination, and is preferably an ester, and even more preferably ethyl acetate.

The applicant company recommends using ethyl acetate as the extraction solvent since, as will be exemplified hereinafter, of all the solvents tested, it proved to be the most effective and is moreover relatively not very toxic.

The extraction solvent can be removed from the organic fraction, preferably by evaporation, for example under vacuum or at reduced pressure, by means of which the oleoresin is obtained.

As will also be exemplified hereinafter, the repeated extraction with ethyl acetate, by exhausting the *Chlorella vulgaris* biomass containing 11% of dry matter prepared in the previous step of the method in accordance with the invention, makes it possible to concentrate the lutein by a factor of 5 to 10 and to achieve extraction yields of about 70%.

Thus, in certain embodiments of the method according to the invention, step 2 comprises at least one step of extracting the cell lysate with a polar solvent, preferably ethyl acetate, it being possible for said extracting step to be repeated. The extracting step can be repeated until a lutein yield of at least 50%, preferably at least 60%, or even at least 65%, by weight relative to the weight of lutein initially present in the cell lysate obtained in step 1 is obtained. The extracting step can thus be repeated from 2 to 8 times, typically 5 times.

The polar solvent/cell lysate volume ratio at each extracting step can range from 1:3 to 3:1. For example, a volume ratio of approximately 1:1 can be used.

The organic fractions (supernatants) can be combined and the polar solvent can be removed, at least partially, by evaporation, preferably under vacuum or under pressure, thus resulting in the obtaining of the oleoresin.

Optionally, since water is a limiting factor, the applicant company also recommends adding a step of concentrating the cell lysate (for example by centrifugation) before carrying out the extraction with the polar solvent, since this makes it possible to increase the overall extraction yield by at least 10%. The extraction can also be envisioned using a dehydrated matrix.

The concentrating of the lysed biomass containing 24% of dry matter thus makes it possible to obtain an extraction yield of 80%.

Thus, in certain embodiments of the method according to the invention, the cell lysate obtained in step 1 is concentrated, preferably to a dry matter content of greater than 15% by weight, preferably ranging from 20% to 30% by weight, before step 2 of preparing the oleoresin is carried out. Typically, the cell lysate can be concentrated to a dry matter content of approximately 22% to 26%, for example 24%. This concentrating step can be carried out by centrifugation.

The third step of the method in accordance with the invention consists of extracting the oleoresin obtained in step 2) with a nonpolar solvent, in this case a fluid at supercritical pressure, in order to obtain a fraction rich in nonpolar lipids, mainly consisting of triglycerides, and an insoluble fraction rich in lutein.

The insoluble fraction rich in lutein, in other words the composition rich in lutein, corresponds to the fraction of oleoresin which has not been entrained by the fluid at supercritical pressure.

The fraction rich in nonpolar lipids, mainly consisting of triglycerides, corresponds to the fraction which is entrained by the nonpolar solvent at supercritical pressure and which is therefore soluble, under the temperature and pressure conditions used, in said solvent.

The third step of the method enables the selective extraction of the nonpolar lipids, the extract then being fractionated by evaporation of the solvent which is condensed and recycled, with recovery of a paste (commonly called a "concrete") rich in nonpolar lipids, mainly consisting of triglycerides; the residue, which is insoluble in the fluid at supercritical pressure, is rich in lutein, which is thus highly concentrated and recovered with a high yield relative to the initial biomass after removal of the fluid at supercritical pressure residually present in this residue.

It is known that a fluid in the supercritical state, i.e. in a state characterized either by a pressure and a temperature that are respectively above the critical pressure and temperature in the case of a pure substance or by a representative point (pressure, temperature) located outside the envelope of the critical points represented on a diagram (pressure, temperature) in the case of a mixture, exhibits, for very many substances, a high solvent power that bears no comparison with that observed in this same fluid in the compressed gas state; the same applies to the "subcritical" liquids, i.e., liquids in a state characterized either by a pressure greater than the critical pressure and by a temperature less than the critical temperature in the case of a pure substance, or by a pressure greater than the critical pressures and a temperature less than the critical temperatures of the constituents in the case of a mixture.

For linguistic convenience, common practice means that the term "compressed fluid" is used for any fluid brought to a pressure substantially greater than atmospheric pressure; the term "fluid at supercritical pressure" is used for fluid brought to a pressure greater than its critical pressure, i.e., either an actual supercritical fluid, or a liquid termed "subcritical" as defined above; likewise, the term "liquefied gas" is used for a liquid consisting of a compound which is in the gas state at atmospheric pressure and at ambient temperature, brought to a pressure and to a temperature which are less than its critical pressure and its critical temperature, respectively.

The considerable and modulable variations in the solvent power of fluids at supercritical pressure are used in many methods of (solid/fluid) extraction, of (liquid/fluid) fractionation, of analytical or preparative chromatography, and of treatment of materials (ceramics, polymers, etc.); chemical or biochemical reactions are also carried out in such solvents.

It should be noted that the physicochemical properties of carbon dioxide and also its critical coordinates (critical pressure: 7.4 MPa and critical temperature: 31° C.) make it the preferred solvent in many applications, especially since it does not show any toxicity and is available very cheaply in very large amounts; carbon dioxide, a nonpolar solvent, brought to supercritical pressure sometimes has added to it a co-solvent consisting of a polar organic solvent which will notably modify the solvent power, especially with respect to molecules having a certain polarity, ethanol often being used for this purpose.

However, some compounds are more favorably extracted with a light hydrocarbon having between 2 and 5 carbon atoms, and more favorably between 2 and 4 carbon atoms, at supercritical pressure.

As is known to those skilled in the art, extraction with a fluid at supercritical pressure produces extracts of very high quality which are increasingly used in many applications.

One of the main advantages of methods using fluids at supercritical pressure lies in the ease with which the solvent (the fluid) can be separated from the extracts and solids.

One of the other important advantages of supercritical fluids lies in their "adaptable" selectivity with respect to the constituents of a mixture. This very high selectivity is linked to the particular properties of supercritical fluids, and particularly to those of carbon dioxide at supercritical pressure: the solvent power can be finely regulated by adjusting the pressure and the temperature of the fluid. It has been found that "mild" conditions are the most selective since the solvent is all the more selective the lower its solvent power.

Thus, in certain embodiments of the method according to the invention, in step 3), the nonpolar solvent in the form of a fluid at supercritical pressure is brought to a pressure of between 10 and 50 MPa, more preferentially between 25 and 40 MPa, and to a temperature of between 35 and 90° C., and preferentially between 40 and 70° C. In other embodiments, in step 3), the nonpolar solvent in the form of a fluid at supercritical pressure is carbon dioxide.

While carrying out step 3), the applicant company preferably uses pure carbon dioxide, rather than carbon dioxide to which has been added a co-solvent that would increase its solvent power, and chooses an operating pressure of between 10 and 50 MPa, more preferentially between 25 and 40 MPa, and a temperature of between 35 and 90° C., and preferentially between 40 and 70° C.

By way of example, step 3) can be carried out using $CO_2$ at a pressure of 25 to 30 MPa, typically approximately 28 MPa, and at a temperature of 40° C. to 50° C., typically approximately 45° C.

Thus, the applicant company has found that it is possible to selectively extract the nonpolar lipids, of triglyceride type, from a concrete obtained during step 3 of the method in accordance with the invention, without extracting the lutein which will thus be highly concentrated in the nonextracted raffinate.

In one particular embodiment, the method according to the invention comprises one or more (1, 2, 3, 4, 5 or 6) of the following characteristics:
- the microalgae are of the *Chlorella* genus, and more particularly of the *Chlorella vulgaris* species, and/or
- step 1) comprises preparing a cell lysate by milling from a microalgal biomass having a dry matter content ranging from 10% to 15%, typically approximately 11% by weight, and/or
- the cell lysate obtained in step 1 is concentrated so as to have a dry matter content greater than 15%, preferably ranging from 20% to 30% by weight, and/or
- step 2) comprising at least one step of extracting the cell lysate with a polar solvent, preferably ethyl acetate, and removing the polar solvent from the organic phase(s) obtained so as to obtain the oleoresin, and/or
- in step 2), the extracting step is repeated until a lutein extraction yield of at least 50% by weight relative to the weight of lutein initially contained in the cell lysate is obtained, and/or
- in step 3), the oleoresin obtained in step 2) is extracted with $CO_2$ at supercritical pressure, preferably at a pressure of between 10 and 50 MPa, more preferably between 25 and 40 MPa, and at a temperature of between 35 and 90° C., preferably between 40° C. and 70° C.

It goes without saying that the method according to the invention may comprise one or more steps in addition to those previously mentioned, for example a step of packaging the lutein-enriched composition obtained in step 4).

A subject of the invention is also a lutein-enriched composition obtained by means of the method according to the invention.

An additional subject according to the invention is the use of the lutein-enriched composition according to the invention for preparing a food supplement or a pharmaceutical composition. The food supplement and the pharmaceutical composition according to the invention may be intended for humans or for animals.

A subject of the invention is also a method for preparing a composition comprising lutein, chosen from a food supplement and a pharmaceutical composition, said method comprising:
a) preparing a lutein-enriched fraction from a microalgal biomass by carrying out the method according to the invention, and
b) obtaining said composition from the lutein-enriched fraction obtained in step a).

Step b) generally comprises mixing the lutein-enriched fraction with one or more excipients or carriers which are acceptable from a food and/or pharmaceutical point of view, so as to obtain the desired food supplement or the desired pharmaceutical composition. The food supplement or the pharmaceutical composition may be in the form of a powder, a tablet, a suspension, a syrup or an oral solution.

The lutein-enriched fraction can also be used for the preparation of a food intended for feeding humans or animals. A subject of the invention is also a method for preparing a food, said method comprising:
a) preparing a lutein-enriched fraction from a microalgal biomass by carrying out the method according to the invention, and
b) obtaining said food from the lutein-enriched fraction obtained in step a).

Step b) generally comprises mixing the lutein-enriched composition with one or more food ingredients and also steps such as cooking or cooling steps.

The invention will be understood more clearly by means of the following examples, which are intended to be illustrative and nonlimiting.

Example 1

Preparation of a Lutein-Concentrated Oleoresin from a *Chlorella vulgaris* Biomass

Step 1: Preparation of a *Chlorella vulgaris* Biomass with a Dry Matter Content of 11% to 12%

Using conventional fermentation in a photobioreactor, it is easy to obtain, at the end of fermentation, a biomass which has a concentration of microalgae of about 78 g/l. Said biomass is then concentrated by centrifugation in a Westfalia model NA7 centrifuge. The biomass is thus concentrated to approximately 120 g/l.

Step 2: Cell Milling

The microalgal biomass thus cultured and then concentrated according to the operating conditions of step 1 is then treated using a Netzsch Labstar agitator bead mill system.

6 liters of biomass containing 12% of dry matter, recovered during step 1, were treated in recirculation mode.

The product therefore undergoes repeated passes through the 0.54-liter milling chamber, 85% filled with ceramic beads of Zeta bead type (Netzsch) 600 µm in diameter. These beads are agitated at a peripheral speed of 12 m/s, which makes it possible to mill virtually all the microalgal cells in 2 h. The quality of the milling is monitored by microscopic observation until no cell is visible in the field of the microscope.

In order to limit the increase in temperature of the product, the milling chamber has a jacket which makes it possible to maintain cold conditions. The mill feed tank is also cooled by a recirculation of cold water at 4° C. supplied by a Julabo type F32 cryostat.

The results of assaying the total carotenoids obtained during this cell milling step are presented in FIG. 1. FIG. 1 presents the assaying of the total carotenoids (carotene and lutein) of *Chlorella vulgaris* before and after milling (mass % relative to the dry weight). The cell milling generates a reasonable 10% lutein loss and 20% carotene loss.

Step 3: Extraction with Solvent

The milled microalgal material obtained following step 2 is then diluted with solvents of various polarities, such as esters, including ethyl acetate, propyl acetate and butyl acetate, ketones such as cyclohexanone and a nonpolar solvent such as hexane. Each solvent was tested alone, in a 1:1 (V biomass/V solvent) volume ratio.

The extraction is then carried out with agitation, in the dark and at ambient temperature for one hour, all of the manipulation being carried out in polypropylene tubes.

After 1 hour of contact, the mixture is separated by centrifugation for 15 min at 20,000 g in a Beckman Coulter Allegra 64R centrifuge. The carotenoid assays were carried out on the supernatant of each solvent tested after a single extraction.

The extraction yield results are presented in FIG. 2.

FIG. 2 presents the total carotenoid (lutein and carotene) extraction yield for various solvents: ethyl acetate (purity>99.5%), propyl acetate (purity>99.5%), hexane (purity>95%) and cyclohexane (purity>95%). Y-axis: extraction percentage.

The best lutein extraction is obtained with ethyl acetate, propyl acetate and cyclohexanone. These tests carried out in a single extraction enable the recovery of approximately 40% of lutein.

Contrary to propyl acetate, cyclohexanone and ethyl acetate have very good extraction yields for carotenes.

This screening also demonstrates that, the longer the aliphatic chain of the ester, the more the lutein extraction yield tends to decrease; this result therefore orients toward the characteristics of the solvent to be used.

Although ethyl acetate and cyclohexanone show very similar extraction yields, ethyl acetate is preferred since this solvent is just as efficient as cyclohexanone but is especially less toxic.

Step 4: Concentration of a Milled Cell Material

A part of the milled cell material obtained in step 2 is concentrated by centrifugation in a Beckman Coulter J20XP rotor JLA at 6000 g for 3 min.

The preparation of the oleoresin was carried out on 3 different samples:
- biomass milled, then concentrated by centrifugation (24% of dry matter),
- biomass milled, not concentrated (11% of dry matter), and
- a control not milled, not concentrated (11% of dry matter).

Step 5: Preparation of the Oleoresin—Extraction with Ethyl Acetate by Exhaustion A 1-to-1 volume ratio of milled biomass and of ethyl acetate (min purity 99.8%) are mixed in a 1-liter polypropylene flask resistant to chemical products.

This mixture is then stirred, in the dark and at ambient temperature. After 1 hour of contact, the mixture is separated by centrifugation in a Beckman Coulter J20XP rotor JLA for 15 min at 12,227 g.

The supernatant thus obtained (approximately 0.4 liter) is put aside in a flask in the dark. With regard to the pellet, it is again taken with solvent. The uptake volume is identical to the volume previously aliquoted.

This operation is carried out 5 times on the same biomass pellet. Still in the dark, the 5 supernatants thus obtained are then combined in one fraction (F) which is analyzed.

FIG. 3 presents the lutein and carotene extraction yields using ethyl acetate of the 3 fractions obtained during the extraction by exhaustion of the biomasses prepared in step 4, i.e., of the milled biomasses (having a dry matter content (DM) of 24% and of 11%) and of the non-milled biomass.

The best extraction yields reach 80% lutein recovery and 90% carotenoid recovery for the sample of biomass containing 24% of DM.

After one extraction, there is already a 40% recovery of lutein (1,3), but after 5 successive extractions, the yield reaches 70%.

This graph also shows that the yields are 10% higher on the concentrated biomass (DM at 24%) than on the initial biomass (DM at 11%). The reaction yield is therefore limited by the presence of water.

The total absence of lutein and of carotene on the non-milled control demonstrates the importance of the cell lysis for the recovery of the molecules of interest.

Step 6: Preparation of the Oleoresin—Concentration of the Total Carotenoids

The various fractions F prepared in step 5 are then transferred into a 2-liter amber round-bottomed flask which is connected to a Buchi Switzerland rotary evaporator under vacuum, of Rotavapor R-215 type.

The evaporation of the solvent is then carried out for 2 h at a vacuum of 200 mbar and at 50° C.

The various results obtained are compiled in FIG. 4 which shows the lutein contents (mass % relative to the dry weight) in the biomasses and the oleoresins.

The oleoresin final dry matter contents are from 65% to 80% and the amount of lutein is in the region of 2 to 3 g for 100 g of dry oleoresin.

The extraction of an oleoresin from a concentrated milled *Chlorella vulgaris* material containing 24% of DM enables a 7-fold concentration of the lutein.

Example 2

Extraction of an Oleoresin Rich in Lutein with a Supercritical Fluid

Step 1: Preparation of the Cell Lysate

The biomass is in the form of an aqueous suspension of *Chlorella vulgaris* lysed according to the conditions of Example 1. The measurement of the dry matter content and the quantitative analysis of the pigments are given in Table 1 below.

TABLE 1

|  | Method | Quantification |
| --- | --- | --- |
| Dry matter | Weighing on desiccator | 12.1% dry matter |
| Total carotenoids | UV spectrophotometer | 9.9 mg/g dry matter |
| Chlorophyll A | UV spectrophotometer | 19.01 mg/g dry matter |
| Chlorophyll B | UV spectrophotometer | 8.93 mg/g dry matter |
| Lutein | HPLC | 2.89 mg/g dry matter |
| Carotenes | HPLC | 0.30 mg/g dry matter |

Step 2: Obtaining the Oleoresin

The lysed biomass is mixed with ethyl acetate in a proportion of 1050 g of biomass, containing 1260 mg of total carotenoids, including 368 mg of lutein, and 500 g of ethyl acetate in a 3-liter flask with a mechanical stirrer for two hours. The mixture thus obtained is decanted by centrifugation; the supernatant is recovered and the pellet is subjected to a second extraction.

This second extraction is carried out under the same conditions as previously, once again using 500 g of ethyl acetate. The mixture obtained is decanted by centrifugation; the supernatant is recovered and the pellet is subjected to a third extraction under the same conditions as the second extraction.

And so on until five extraction operations have been carried out and 2500 g of ethyl acetate have been used.

The supernatants thus collected are combined into one solution which is then evaporated in a rotary evaporator under vacuum, resulting in the recovery, on the one hand, of the solvent and, on the other hand, of an oleoresin.

The mass of oleoresin thus obtained is 11.95 g and contains 550 mg of total carotenoids, including 310 mg of lutein.

Step 3: Extraction with Supercritical Fluid

The oleoresin obtained during the previous step is placed in a cylindrical basket closed by two sintered metal filters, which is itself placed in a pressurized container connected to a pump fed with liquid $CO_2$ and a flow rate of 3 kg/h, the fluid thus compressed at 28 MPa then being heated to 45° C. and introduced into the pressurized container containing the basket loaded with the oleoresin.

The pressure of the fluid leaving the pressurized container after having been loaded with solute on contact with the oleoresin is then reduced to 5 MPa in two cyclonic separators maintained at 45° C. The solutes are separated and recovered in the separators and the $CO_2$ is discharged into the atmosphere.

After two hours of extraction, the pressurized container is depressurized and opened and the basket is recovered. The residue contained in the basket is in the form of a dry powder which has a mass of 1.75 g containing 218 mg of lutein, i.e., a mass content of lutein of 12% relative to the total weight of the residue.

The invention claimed is:

1. A method for preparing a composition enriched in lutein from a microalgal biomass, the method comprising the steps of:
    a) preparing a cell lysate from the microalgal biomass and concentrating said cell lysate to a dry matter content of more than 15% by weight,
    b) treating the cell lysate with a polar solvent to obtain an oleoresin containing lutein and lipids from the initial microalgal biomass,
    c) extracting the oleoresin obtained in step b) with a nonpolar solvent in the form of a supercritical fluid of $CO_2$ at a pressure of 25 MPa to 40 MPa and at a temperature from 35° C. to 90° C. to obtain a nonpolar lipid fraction containing triglycerides and an insoluble fraction enriched in lutein, and
    d) recovering the insoluble fraction enriched in lutein.

2. The method of claim 1, wherein the microalgae belongs to the *Chlorella* family.

3. The method of claim 1, wherein the polar solvent of step b) is selected from the group consisting of methanol, ethanol, n-propanol and isopropanol, butanol and isobutanol, esters and ketones, taken alone or in combination.

4. The method of claim 1, wherein the polar solvent of step b) is selected from the group consisting of ethyl acetate, propyl acetate, butyl acetate, acetone, cyclohexanone, methyl ethyl ketone, methyl isobutyl ketone and combinations thereof.

5. The method of claim 1, wherein the nonpolar solvent in the form of the supercritical fluid is brought to a pressure of 25 MPa to 40 MPa, and to a temperature of 40° C. to 70° C.

6. The method of claim 2, wherein in step a), the cell lysate is obtained by milling the microalgal biomass of the *Chlorella* family.

7. The method of claim 1, wherein the cell lysate obtained in step a) is concentrated to a dry matter content of 20% to 30% by weight.

8. The method of claim 1, wherein step b) comprises at least one step of extracting the cell lysate with the polar solvent, and removing the polar solvent from the resulting organic phase.

9. The method of claim 1, wherein the polar solvent is ethyl acetate.

10. A method for preparing a composition selected from a pharmaceutical composition, a food supplement and a food, the method comprising the steps of:
    a) obtaining a lutein-enriched fraction by the method of claim 1, and
    b) preparing the pharmaceutical composition, food supplement or food from said lutein-enriched fraction of step a).

11. A method for preparing a composition enriched in lutein from a biomass of microalgae belonging to the *Chlorella* genus, the method comprising the steps of:
    a) preparing a cell lysate from the microalgal biomass by milling and concentrating said microalgal biomass to a dry matter content of 20% to 30% by weight,
    b) treating the cell lysate with a polar solvent selected from ethyl acetate, propyl acetate, butyl acetate, and cyclohexanone to obtain an oleoresin containing lutein and lipids from the microalgal biomass, and optionally repeating step b),
    c) extracting the oleoresin obtained in step b) with a nonpolar solvent in the form of a supercritical fluid of $CO_2$ at a pressure of 25 MPa to 40 MPa and at a temperature from 40° C. to 70° C. to obtain a nonpolar lipid fraction containing triglycerides and an insoluble fraction enriched in lutein, and
    d) recovering the insoluble fraction enriched in lutein.

12. The method of claim 1, wherein the nonpolar solvent in the form of the supercritical fluid of $CO_2$ is brought to a pressure of 35 MPa to 40 MPa.

13. The method of claim 11, wherein the nonpolar solvent in the form of the supercritical fluid of $CO_2$ is brought to a pressure of 35 MPa to 40 MPa.

14. The method of claim 11, wherein the polar solvent is ethyl acetate.

* * * * *